United States Patent [19]

Kirkovits et al.

[11] Patent Number: 5,079,164

[45] Date of Patent: Jan. 7, 1992

[54] MICROORGANISM OF THE SPECIES *BACILLUS CIAGUANS*

[75] Inventors: August E. Kirkovits, Stronegg; Helga Edlauer, Laa an der Thaya, both of Austria

[73] Assignee: Jungbunzlauer Aktiengesellschaft, Austria

[21] Appl. No.: 485,451

[22] Filed: Feb. 27, 1990

[30] Foreign Application Priority Data

Mar. 10, 1989 [AT] Austria ................................. 555/89

[51] Int. Cl.⁵ ........................... C12P 7/56; C12R 1/07
[52] U.S. Cl. ................... 435/252.5; 435/139; 435/832
[58] Field of Search ................ 435/252.5, 139, 832

[56] References Cited

U.S. PATENT DOCUMENTS

Re. 30,965  6/1982  Hitzman ........................ 435/252.5

FOREIGN PATENT DOCUMENTS 0040093  3/1983  Japan ................................... 435/139

*Primary Examiner*—Herbert J. Lilling
*Attorney, Agent, or Firm*—Paul & Paul

[57] ABSTRACT

Proposed is a microorganism of the species *Bacillus coagulans* DSM 5196 as well as a method of producing L(+)-lactic acid in which said microorganism is employed.

1 Claim, No Drawings

MICROORGANISM OF THE SPECIES *BACILLUS CIAGUANS*

The invention relates to a microorganism of the species Bacillus coagulans and to a method of producing optically pure L(+)-lactic acid by cultivating this microorganism in or on a suitable nutrient medium, whereby a culture broth containing L(+)-lactic acid is obtained, the L(+)-lactic acid formed preferably being isolated from the culture broth.

Nutrient media suitable for the production of lactic acid usually contain various nitrogen sources in addition to various growth substances such as trace elements and vitamins and useful carbohydrates, preferred organic nitrogen sources being yeast extract or corn steep liquor.

The production of lactic acid from various carbohydrate-containing starting materials with addition of the most diverse nitrogen sources, phosphor compounds, vitamins and other production-promoting substances has been known since the turn of the century.

One of the first publications relating to this process is FR-PS 679 418 dating from 1929. Subsequently, EP-PS 69 291 discloses the use of yeasts and EP-A-0 113 215 published in 1984 describes the production of lactic acid by bacteria of the species Lactobacillus. More recent publications deal with process optimations mainly characterized by the introduction of special nitrogen sources, such as EP-PS 0 266 258 (1988). The lactic acid-producing microorganism again belongs to the genera Lactobacillaceae.

None of these methods, however, have been able to satisfy the increasing demand for optically pure L(+)-lactic acid, which in addition to the use in the food and stimulant industry results from the use of lactic acid for the production of biodegradable plastics materials.

The problem thus consisted in developing a method of producing optically pure L(+)-lactic acid with particular minimation of nitrogen addition and fermentation time. At the same time, a reaction of glucose as well as sucrose was aimed at, regardless of whether the materials involved were pure raw materials or e.g. molasses.

To this end, a concerted isolation of lactic acid-forming bacteria from vegetable matter was carried out.

In this, a microorganism belonging to the family of Bacillaceae was isolated from silage. Surprisingly, it was possible to increase the metabolic output of the bacterium by concerted enrichment methods to such an extent that it is capable of converting carbohydrates, preferably glucose or sucrose, to L(+)-lactic acid, in contrast to methods of prior art at starting concentrations of more than 140 g/l.

Investigations of this microorganism according to the invention resulted in its identification as *Bacillus coagulans* of the following taxonomic characteristics:

Gram-positive rods of the dimensions 1.5 to 4×0.4 to 0.8 um;
formation of ellipsoid or cylindrical spores; immobile;
aerobic to facultatively anaerobic;
growth at 30° to 60 ° C., optimum temperature at 48° to 54° C.;
growth at pH value of 4.5 to 7.0, optimum pH range between 5.8 and 6.2;
catalase: positive;
acid formation from
    D-glucose: positive
    L-arabinose: negative
    D-xylose: negative
    D-mannitol: negative
    lactose: positive
gas formation from glucose: negative
desamination of phenyl alanine: negative
reduction of nitrate: negative
utilization of citrate or propionate: negative
degradation of
    starch: negative
    caseine: negative
    gelatine: negative
    tyrosine: negative
    DNA: positive
formation of indole: negative
fermentation behavior: homofermentative formation of L(+) lactic acid The strain characterized by foregoing data was deposited at Deutsche Sammlung f/ r Mikroorganismen (German Micrororganism Collection) Mascheroder Weg 1B, D-3300 Braunschweig according the provisions of the Budapest Treaty on 31/1/1989 under the accession number DSM 5196.

It was found that the microorganism according to the invention is capable of forming lactic acid at temperatures of up to about 60° C.; a further feature of the method according to the invention thus resides in that the cultivation of the microorganism is carried out at temperatures in the range of from 30° to 60° C., preferably of from 48° to 54° C., in particular at about 52° C.

It was further found that at elevated temperatures, in particular of between 50° and 60° C., sterile operation is not necessary and that in particular, sterilization of the nutrient medium (e.g. 15 minutes of heating to 121° C.) can be omitted. A further feature of the method according to the invention further resides in the measure that the cultivation of the microorganism is carried out under non-sterile conditions.

The cultivation of the microorganism is further conveniently carried out under aerobic conditions.

It is disclosed e.g. in EP-A-0 266 258 that it has not been possible up to the present to operate with starting concentrations of sugar of more than 140 g/l. As already mentioned initially, the microorganism according to the invention is capable of processing higher sugar concentrations.

A further feature of the invention thus resides in the fact that the cultivation of the microorganism is carried out in or on a medium whose sugar starting concentration ranges above 140 g/l, preferably between 180 and 200 g/l, in particular at about 190 g/l.

Technically, this means above all that the entire amount of sugar to be fermented can be employed, that the method according to the invention can thus be operated as a batch process, in contrast to known processes such as e.g. the one according to EP-A 0 072 010, wherein sugar is added continuously or discontinuously during cultivation.

It was further found that the nutrient medium in the method according to the invention must have a much lower content of organic and inorganic nitrogen than usual up to now.

Further features of the method according to the invention are thus that the cultivation of the microorganism is carried out in or on a medium whose content of corn steep liquor amounts to about 30 g/l at most and that of yeast extract to about 3 g/l, resulting in a content of amino nitrogen of 0.15 to 0.4 g/l, on the one hand, and that the cultivation of the microorganisms is carried out in or on a medium containing about 3 g/l ammonium phosphate at most, on the other hand.

As a result, the L(+)-lactic acid formed can be isolated and recovered from the culture medium by means of far less elaborate processes than those employed up to now. So, for instance, the simple neutralization by means of Ca(OH)$_2$ will cause the formation of crystals of Ca(+)-lactate.

It may be necessary to use antifoaming agents in the method according to the invention.

The invention is explained in detail with reference to the following examples:

EXAMPLE 1

Isolation and improvement of the strain *Bacillus coagulans*

Vegetable matter was incubated with exclusion of air at 50° C. for 7 days, then taken up in sterile water, shaken and filtered. The resulting filtrate was diluted to such an extent that individual colonies formed following the inoculation of Petri dishes containing medium 1 and incubation at 50° C.±2° C.

Medium 1: (Commercial product Nutrient Agar CM3 Oxoid or Difco 1816 Standard 2 Nutrient Agar or Standard 2 Nähr Agar Merck 7883)

| Meat extract | 1 g/l |
|---|---|
| Yeast extract | 2 g/L |
| Peptone | 5 g/l |
| NaCl | 5 g/l, pH 7.4 |
| Glucose | 10 g/l |
| Sucrose | 10 g/l |
| Agar | 15 g/l |
| Solvent | aqua dest. |

After 48 hours, about 200 colonies were isolated and examined as to their fermentation output: 10 ml medium 2 each were inoculated with the respective isolate and bred for 5 days at 50° C.±2° C. The lactic acid concentration was then determined enzymatically in each batch.

Medium 2

| Sucrose | 120 g/l |
|---|---|
| (NH$_4$)$_2$HPO$_4$ | 1.5 g/l |
| CaCO$_3$ | 70 g/l |
| Yeast autolysate | 5 g/l |
| Solvent: | aqua dest. |

The isolate having the highest content in L(+)-lactic acid was used for the further selection work. This isolate was used for inoculating flasks with medium 2, sucrose was replaced by glucose and the concentration of carbohydrates was increased by 10 g/l. Incubation was maintained for 4 days at 50° C. This process was repeated until 190 g/l of sucrose or glucose were converted into to L(+)-lactic acid within 4 days in each case.

The strain was preserved by storing the cultures on medium 1 at −15° C.

EXAMPLES 2 TO 5

Production of L(+)-lactic acid

Cultures prepared according to Example 1 were transferred to Medium 3, care being taken not to employ an inoculation volume of less than 1 percent.

Medium 3:

| Carbohydrates: | 190 g/l based on glucose equivalent (in Examples 2 + 4: sucrose in Examples 3 + 5: glucose) |
|---|---|
| inorganic nitrogen: | 1.5 g as (NH$_4$)$_2$HPO$_4$ |
| organic nitrogen: | 3 g/l as yeast autolysate (in Examples 2 + 3), an average content of amino nitrogen of 4.8 to 5.8 percent and/or protein (N × 6.25) of 56 to 62 percent being assumed at a dry matter of 94 to 98 percent, |
| or | 30 g/l as corn steep liquor (in Examples 4 + 5) an average content of amino nitrogen of 2 to 3 percent or protein (N × 6.25) of 43 to 49 percent being assumed at a dry matter of 45 percent. |

The production solution was kept at a constant temperature of 52° C. by appropriate measures and stirring was effected for optimum mixing of the medium. Adjustment of the pH value to 6.0 was effected by addition of the lime milk.

RESULTS

| CARBO-HYDRATE SOURCE | ORGANIC NITROGEN SOURCE | FERMENTATION TIME (Hours) | L(+)LACTIC ACID (g/l) | OPTICAL PURITY (%L(+)) |
|---|---|---|---|---|
| Example 2: Sucrose | Yeast autolysate | 39 | 140 | 99.8 |
| Example 3: Glucose | Yeast autolysate | 49 | 133 | 99.8 |
| Example 4: Sucrose | Corn steep liquor | 43 | 135 | 98.5 |
| Example 5: Glucose | Corn steep liquor | 51 | 134 | 98.7 |

The portion of 1 to 1.5 percent of D(−)-lactic acid in Examples 4 and 5 is attributable to the lactic acid of corn steep liquor which is usually present in the form of a racemic compound.

We claim:

1. A biologically pure culture of a microorganism of the species *Bacillus coagulans* DSM 5196, said microorganism being capable of producing L(+)-lactic acid upon fermentation in an aqueous nutrient medium containing assimilable sources of carbohydrates, nitrogen and protein, wherein the medium contains a starting concentration of sugar more than 140 g/l.

* * * * *

UNITED STATES PATENT OFFICE
CERTIFICATE OF CORRECTION

Patent No.     5,079,164          Dated    January 7, 1992

Inventor(s) August E. Kirkovits and Helga Edlauer

It is certified that error appears in the above-identified patent and that said Letters Patent is hereby corrected as shown below:

Column 2, Line 18, delete "f/r Mikroorganismen" and substitute therefore --für Mikrorganismen--.

Column 2, Line 20, after the word according, insert the word --to--.

Column 2, Line 39, delete the word "aerobic" and insert therefore --anaerobic--.

Signed and Sealed this

Twenty-seventh Day of April, 1993

Attest:

MICHAEL K. KIRK

*Attesting Officer*          *Acting Commissioner of Patents and Trademarks*